(12) United States Patent
Kindlein et al.

(10) Patent No.: US 7,399,269 B2
(45) Date of Patent: Jul. 15, 2008

(54) PROCESS, CONTROL PROGRAM, TREATMENT PLANNING SYSTEM AND CONTROL SYSTEM, AND DOSE MEASURING SYSTEM FOR BRACHYTHERAPY

(75) Inventors: Johann Kindlein, Oberhausen (DE); Leo Hovestadt, Veenendaal (NL)

(73) Assignee: Nucletron B.V., Veenedaal (NL)

( * ) Notice: Subject to any disclaimer, the term of this patent is extended or adjusted under 35 U.S.C. 154(b) by 0 days.

(21) Appl. No.: 10/307,355

(22) Filed: Dec. 2, 2002

(65) Prior Publication Data
US 2004/0106840 A1    Jun. 3, 2004

(51) Int. Cl.
*A61N 5/00* (2006.01)
(52) U.S. Cl. ......................................................... 600/3
(58) Field of Classification Search ............... 600/1–8, 600/44, 427, 407; 128/897–898; 348/7
See application file for complete search history.

(56) References Cited

U.S. PATENT DOCUMENTS 5,391,139 A * 2/1995 Edmundson ............... 600/7
6,129,670 A * 10/2000 Burdette et al. ............ 600/427
6,311,084 B1 * 10/2001 Cormack et al. ........... 600/411
6,327,490 B1 * 12/2001 Spetz ........................ 600/427
6,431,175 B1 * 8/2002 Penner et al. ............... 128/899
6,438,401 B1 * 8/2002 Cheng et al. ................ 600/407
2003/0212302 A1 * 11/2003 Rozenfeld et al. ............ 600/1

* cited by examiner

*Primary Examiner*—Samuel G Gilbert
(74) *Attorney, Agent, or Firm*—Birch, Stewart, Kolasch & Birch, LLP

(57) ABSTRACT

The invention relates to a process for brachytherapy by using a dose measuring system, wherein, in at least one point of an area subjected to radiation treatment, the individual radiation dose contribution from at least one dwell position of at least one radiation source is measured in real time, the thus obtained measured dose value is compared with the corresponding value calculated by a treatment planning system, and the further course of the treatment is adapted on the basis of the degree of agreement between the measured value and the calculated value. Furthermore, the invention relates to a control program, a treatment control system, a treatment planning system and a dose measuring system.

6 Claims, 1 Drawing Sheet

PROCESS, CONTROL PROGRAM, TREATMENT PLANNING SYSTEM AND CONTROL SYSTEM, AND DOSE MEASURING SYSTEM FOR BRACHYTHERAPY

The present invention relates to a process for achieving quality assurance in the field of brachytherapy, a control program, a treatment planning system and control system, and a dose measuring system.

In the present context of the field of brachytherapy, quality assurance comprises quality assurance on the treatment unit, quality assurance on the treatment planning system, and quality assurance on the treatment procedure. Brachytherapy treatment errors which are difficult to detect can occur in the following areas: patient and treatment planning identification, applicator identification, applicator displacement, correct positioning of the radioactive sources, and treatment times. Treatment errors also comprise reconstruction errors.

Processes for achieving quality assurance in the field of brachytherapy by using a dose measuring system are known. Existing brachytherapy devices receive coordinates of dwell positions and dwell times of radioactive radiation sources from a treatment planning system. Although the individual contributions from the dwell positions reaching a particular point in the treatment area are calculated in the presently marketed treatment planning systems, these values are merely used to calculate the total dose contributions in the different points on a theoretical basis.

The existing treatment planning systems transfer the following parameters to the treatment control stations comprising the treatment control program: patient data, and, concerning the radio-active radiation sources, channel numbers ($C_1$-$C_m$), dwell positions ($X_1$-$X_n$) and dwell times ($T_1$-$T_n$). A remote afterloading control program will execute said prescribed parameters, but no intelligence is implemented to control any applied dose at a particular point within the treatment area on a real time basis. Only the dwell times are controlled.

The existing processes offer no possibility to detect and stop an incorrect administration of radiation, particularly in the initial stage of the treatment. Controlling the most important treatment parameter, i.e. the actual dose which is applied to a point within the treatment area on a real time basis, would provide a highly desired improvement over existing processes for achieving quality assurance in the field of brachytherapy. Presently marketed treatment control programs connected with dose measuring systems enable the practitioner only to measure doses with rectal probes, and to switch off the treatment if the dose value on one of the rectal probes reaches a predetermined limit value. Thus, while existing systems can be used to protect critical organs like the rectum, they cannot be used to achieve real time quality assurance of the treatment, with a view to detecting the above-mentioned treatment errors.

The process for achieving quality assurance in the field of brachytherapy by using a dose measuring system according to the present invention is characterised in that, in at least one point of an area subjected to radiation treatment, (i) the individual radiation dose contribution from at least one dwell position of at least one radiation source is measured in real time, (ii) the thus obtained measured dose value is compared with the corresponding value calculated by a treatment planning system, and (iii) the further course of the treatment is adapted on the basis of the degree of agreement between said measured value and said calculated value.

According to the present invention, the calculated individual dose contributions from the dwell positions at particular point with the treatment area, are individually stored and transferred to a control system of the remote brachytherapy afterloading stepping device, and are compared step by step with the individual dose values measured in real time with the dosimetry system.

According to the invention, the control program of the stepping device not only controls and supervises the afterloading stepping device, but also measures the times of the dosimetry system. Thus, the present process will allow step by step control during the treatment procedure, by automated comparison of the actual measured dose contributions from each source position at a particular point with the doses calculated by the planning system. The treatment planning system used according to the present process will store in a table the individual dose contributions from each source position with respect to a predetermined point within the treatment area, and will transfer these individual dose contributions to the treatment control program, together with the other treatment parameters.

The present process is preferably applied to one of (a) high dose rate afterloading brachytherapy, and (b) pulsed low dose rate afterloading brachytherapy. In the context of the present invention, high dose rate brachytherapy means applying a dose of about 10 Curie and more, and low dose rate brachytherapy means applying doses of less than 1 Curie.

Advantageously, the point of measuring said dose contribution is situated in the actual tissue which is being treated. According to a preferred aspect of the present invention, said tissue is the prostate gland.

Preferably, the at least one individual dose contribution is measured using an instant dose readout dosimeter system, with a probe inserted in the predetermined point in the area subjected to treatment. Advantageously, the process according to the present invention is characterised in that in the least one point, several individual dose contributions ($D_1$-$D_n$) from several dwell positions ($X_1$-$X_n$), each with corresponding dwell times ($T_1$-$T_n$), in several channels ($C_1$-$C_m$), are measured in real time. Furthermore, the calculated value(s) is (are) individually stored and transferred to a treatment control program, and is (are) compared step by step with the measured dose value(s).

The present invention also relates to a control program for a remote brachytherapy afterloading device, which compares the calculated value(s) with the measured value(s) obtained by using the present process. Furthermore, the invention relates to a treatment control system comprising said control program connected with a real time dose measuring system. The invention also provides a treatment planning system for carrying out the above described process.

Finally, the present invention provides a dose measuring system, wherein individual measuring times for (an individual predetermined point(s) in an area treated by brachytherapy are controlled by the present control program, and are equal with dwell position times ($T_1$-$T_n$) of at least one radiation source.

The above-mentioned features and advantages of the present invention are now illustrated in the following description with reference to the enclosed drawings.

Figure 1:
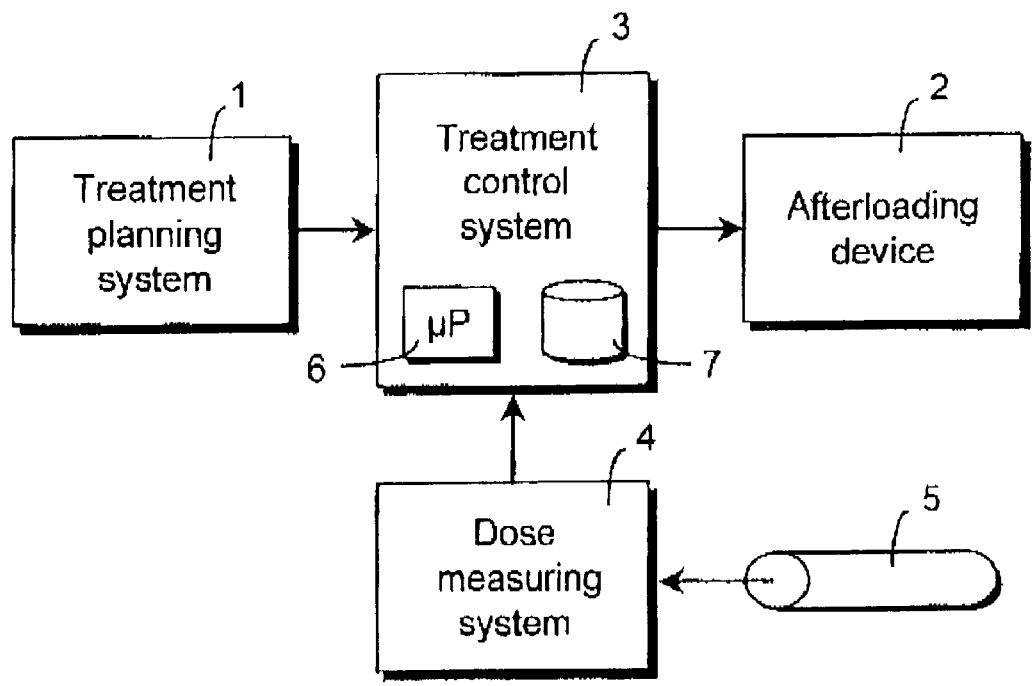
FIG. 1 shows a block diagram of a treatment system for brachytherapy in accordance with the present invention.

As shown in FIG. 1, a treatment system for performing brachytherapy in accordance with the present invention essentially comprises a treatment planning system 1, an afterloading device 2, a treatment control system 3, and a dose measuring system 4.

The treatment planning system 1 generally comprises a computer, such as a personal computer, which is used for treatment planning purposes by a physician or other person applying the brachytherapy treatment. That is, amongst others, for calculating planning parameters such as dwell positions and dwell times of radio-active sources in a plurality of channels of the afterloading device 2.

Afterloading devices for brachytherapy are as such known to those skilled in the art. No further elucidation seems required here.

The treatment planning system 1 connects to a treatment control system 3. The control system 3 operatively connects to the after-loading device 2 for controlling the position of one or a plurality of radiation sources in the channels of the afterloading device 2.

The dose measuring system 4 comprises a measuring probe 5 for measuring the radiation dose at a particular treatment point in an area to be treated.

In accordance with the present invention, the individual radiation dose contribution of at least one radiation source at at least one dwell position is measured by the radiation dose measurement system 4 in real time. The obtained measured dose value is compared with the corresponding value obtained from the treatment planning system 1. To this end, in the embodiment shown, the treatment control system 3 is provided with processor means 6 for comparing the actually measured dose value with the corresponding planned dose value stored in storage means 7.

Figure 2:
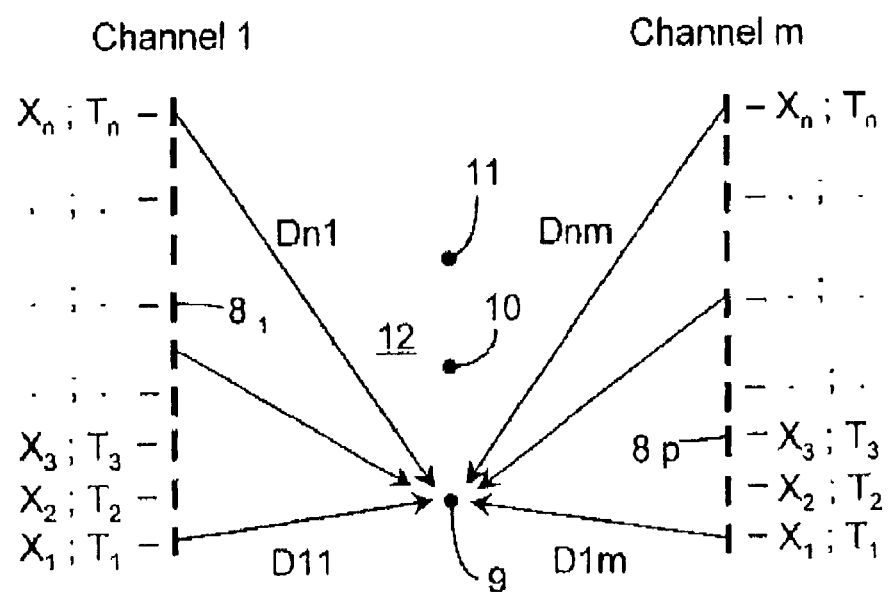
FIG. 2 shows, in a schematic and illustrative manner, radiation dose measuring in accordance with the present invention.

FIG. 2 shows, in a schematic and illustrative manner, a plurality of channels $C_1$-$C_m$, in each of which at least one radiation source $8_1$-$8_p$ can be moved.

During treatment, the radiation source in a particular channel is positioned at several pre-calculated dwell positions $X_1$-$X_n$. At the position of the probe 5, the dose contributions Dnm of the individual radiation sources in the several channels $C_1$-$C_m$ at their various dwell positions $X_1$-$X_n$ are measured in real time. Dnm denotes the dose contribution of a particular radiation source $8_1$-$8_p$ at a particular dwell position $X_1$-$X_n$ in a particular channel $C_1$-$C_m$.

In accordance with the present invention, the measured dose values are compared in real time with the calculated values from the treatment planning system 1 by the processor means 6 in the control system 3, in accordance with a dose control program forming part of the present invention.

If the measured value differs from the calculated value, the control system 3 adapts either one or both the dwell positions $X_1$-$X_n$ and the dwell times $T_1$-$T_n$ of one or a plurality of the radiation sources in the channels $C_1$-$C_m$, in order to meet the planned treatment values as closely as possible.

It will be appreciated that the measuring probe 5 can be positioned at any position 9, 10, 11 in the area 12 to be treated in order to achieve an optimal quality assurance.

The invention claimed is:

1. A process for brachytherapy using a dose measuring system and treatment planning system, said process comprising:
    subjecting at least one point of an area to radiation treatment by positioning at least one radiation source at a plurality of dwell positions, each for an individual dwell time;
    measuring the individual radiation dose contribution from at least one dwell position of said at least one radiation source in real time;
    comparing the obtained measured dose value with a corresponding value calculated by a treatment planning system; and
    adapting a further course of treatment on the basis of a degree of agreement between said measured value and said calculated value;
    wherein several individual dose contributions from several dwell positions, each with corresponding dwell times are measured in real time for several channels.

2. The process according to claim 1, wherein the process is used in one of (a) a high dose rate afterloading brachytherapy, and (b) a pulse low dose rate afterloading brachytherapy.

3. The process according to claim 1, wherein said measuring of said dose contribution is accomplished in an actual tissue being treated.

4. The process according to claim 3, wherein said tissue is a prostate gland.

5. The process according to claim 1, wherein said measuring of said individual dose contribution uses an instant dose read out dosimeter system, with a probe inserted in said at least one point in said area subjected to treatment.

6. The process according to claim 1, wherein calculated dose values are individually stored and transferred to a treatment control program and are compared step by step with said measured dose values.

* * * * *